United States Patent
Mariñas Pardo et al.

(10) Patent No.: US 11,413,314 B2
(45) Date of Patent: *Aug. 16, 2022

(54) PHARMACEUTICAL COMPOSITION FOR DERMATOLOGY AND USES THEREOF

(71) Applicant: NextPhase Therapeutics, Inc, Mercer Island, WA (US)

(72) Inventors: Luis Mariñas Pardo, A Coruña (ES); Manuel Hermida Prieto, A Coruña (ES)

(73) Assignee: NEXTPHASE THERAPEUTICS, INC., Mercer Island, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/252,191

(22) PCT Filed: Jun. 14, 2019

(86) PCT No.: PCT/EP2019/065753
§ 371 (c)(1),
(2) Date: Dec. 14, 2020

(87) PCT Pub. No.: WO2019/238952
PCT Pub. Date: Dec. 19, 2019

(65) Prior Publication Data
US 2021/0244767 A1 Aug. 12, 2021

(30) Foreign Application Priority Data
Jun. 15, 2018 (EP) .................................... 18382430

(51) Int. Cl.
| | |
|---|---|
| *A61K 35/28* | (2015.01) |
| *A61P 17/06* | (2006.01) |
| *A61K 9/00* | (2006.01) |
| *A61K 9/06* | (2006.01) |
| *A61K 9/127* | (2006.01) |
| *A61K 45/06* | (2006.01) |
| *A61K 47/14* | (2017.01) |
| *A61K 47/18* | (2017.01) |
| *A61P 17/00* | (2006.01) |

(52) U.S. Cl.
CPC ............ *A61K 35/28* (2013.01); *A61K 9/0014* (2013.01); *A61K 9/06* (2013.01); *A61K 9/127* (2013.01); *A61K 45/06* (2013.01); *A61K 47/14* (2013.01); *A61K 47/183* (2013.01); *A61P 17/00* (2018.01); *A61P 17/06* (2018.01)

(58) Field of Classification Search
None
See application file for complete search history.

(56) References Cited

FOREIGN PATENT DOCUMENTS

| | | |
|---|---|---|
| WO | 2008/020815 | 2/2008 |
| WO | 2008/155659 | 12/2008 |
| WO | 2017/041133 | 3/2017 |
| WO | 2017/144552 | 8/2017 |

OTHER PUBLICATIONS

Al Delfi et al., "Canine mesenchymal stem cells are neurotrophic and angiogenic: An in vitro assessment of their paracrine activity," *The Veterinary Journal* 217:10-17, 2016.

Ansari et al., "Therapeutic Potential of Canine Bone Marrow Derived Mesenchymal Stem Cells and its Conditioned Media in Diabetic Rat Wound Healing" *Stem. Cell Res. Ther.* 3(3):1-6, 2013.

Arnhold et al., "Isolation and characterization of bone marrow-derived equine mesenchymal stem cells," *Am. J. Vet. Res.* 68(10):1095-1105, 2007.

Caplan, "Mesenchymal Stem Cells," *J. Orthop. Res.* 9:641-650, 1991.

Dennis et al., "A Quadricpotential Mesenchymal Progenitor Cell Isolated from the Marrow of an Adult Mouse," *J. Bone Miner. Res.* 14(5):700-709, 1999.

Dennis et al., "Differentiation Potential of Conditionally Immortalized Mesenchymal Progenitor Cells From Adult Marrow of a $H-2K^b$-tsA58 Transgenic Mouse," *J. Cell. Physiol.* 167(3):523-538, 1996.

Guttman-Yassky et al., "Atopic dermatitis and psoriasis: two different immune diseases or one spectrum?" *Current Opinion in Immunology* 48:68-13, 2017.

Hanifin et al., "Diagnostic Features of Atopic Dermatitis," *Acta Dermatovener (Stockholm) Suppl.* 92A4-41, 1980.

(Continued)

*Primary Examiner* — Nannette Holloman

(74) *Attorney, Agent, or Firm* — Seed IP Law Group LLP

(57) ABSTRACT

The present invention refers to a composition comprising a conditioned cell culture medium obtained or obtainable by a process which comprises culturing a population of mesenchymal stromal cells (MSCs), in which at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%, of said population by number of cells are MSCs obtained from a mammal pertaining to the genus *Canis*, in a nutrient rich liquid prepared for cell culture, preferably a basal media; and collecting the conditioned cell culture medium, wherein preferably the nutrient rich liquid is an animal/human serum-free media or a chemically defined animal/human serum-free and xeno free media designed to grow MSCs, for use in therapy.

10 Claims, 11 Drawing Sheets

(56) References Cited

OTHER PUBLICATIONS

Huang et al., "Rat Extramedullary Adipose Tissue as a Source of Osteochondrogenic Progenitor Cells," *Plast. Reconstr. Surg.* 709:1033-1041, 2002.

Johnstone et al., "In Vitro Chondrogenesis of Bone Marrow-Derived Mesenchymal Progenitor Cells," *Exp. Cell Res.* 238(1):265-212, 1998.

Kisiday et al. "Evaluation of Adult Equine Bone Marrow- and Adipose-Derived Progenitor Cell Chondrogenesis in Hydrogel Cultures," *Orthop. Res.* 26:322-333, 2008.

Kopen et al., "Marrow stromal cells migrate throughout forebrain and cerebellum, and they differentiate into astrocytes after injection into neonatal mouse brains," *Proc. Natl. Acad. Sci. USA* 96:10711-10716, 1999.

Pawitan, "Prospect of Stem Cell Conditioned Medium in Regenerative Medicine," *BioMed Research International* 2014(965849):1-14, 2014.

Seetharaman et al., "Mesenchymal Stem Cell Conditioned Media Ameliorate Psoriasis Vulgaris: A Case Study," *Case Reports in Dermatological Medicine* 2019(8309103):1-5, 2019.

Smith et al., "Isolation and implantation of autologous equine mesenchymal stem cells from bone marrow into the superficial digital flexor tendon as a potential novel treatment," *Equine Vet. J.* 35(1):99-102, 2003.

Takemitsu et al., "Comparison of bone marrow and adipose tissue-derived canine mesenchymal stem cells," *BMC Veterinary Research* 8(150):1-9, 2012.

Toma et al., "Human Mesenchymal Stem Cells Differentiate to a Cardiomyocyte Phenotype in the Adult Murine Heart," *Circulation* 105:93-98, 2002.

Vidal et al., "Cell Growth Characteristics and Differentiation Frequency of Adherent Equine Bone Marrow-Derived Mesenchymal Stromal Cells: Adipogenic and Osteogenic Capacity," *Vet. Surg.* 35:601-610, 2006.

Walter et al., "Mesenchymal stem cell-conditioned medium accelerates skin wound healing: An in vitro study of fibroblast and keratinocyte scratch assays," *Experimental Cell Research* 316:1271-1281, 2010.

Zuk et al., "Multilineage Cells from Human Adipose Tissue: Implications for Cell- Based Therapies," *Tissue Eng.* 7(2):211-228, 2001.

Day 0

Day 9

Day 36

PHARMACEUTICAL COMPOSITION FOR DERMATOLOGY AND USES THEREOF

FIELD OF THE INVENTION

The present invention relates to the fields of development, cell biology, molecular biology and genetics. More particularly, the invention relates to a method of deriving a conditioned media from mesenchymal stem cells obtained from a mammal pertaining to the genus *canis* and uses of such media for the treatment of skin inflammatory disorders such as psoriasis or atopic dermatitis.

BACKGROUND OF THE INVENTION

The skin, once thought to be immunologically sequestered from the body, is now deemed to be an integral part of a multisystem inflammatory axis.

Atopic dermatitis (AD) and psoriasis, especially in their most severe forms, have been linked to a variety of systemic inflammatory disorders and comorbidities. These comorbidities highlight that inflammatory skin diseases of childhood are serious chronic multisystem illnesses and not merely cosmetic conditions.

Atopic dermatitis comorbidities vary by age and length of illness. Some of the most common comorbidities are included in the gold-standard AD diagnostic criteria by Hanifin and Rajka (*Acta Derm Venereol Suppl* (Stockh) 1980; 92:44-47). These criteria include pruritus, chronic or recurrent dermatitis, specific distribution by age (e.g., flexural disease of childhood) and personal and/or family history of atopy, i.e., food allergies, asthma and allergic rhinoconjunctivitis. Minor features include more than a dozen comorbid conditions, including ichthyosis vulgaris; bacterial and viral infections; allergic predisposition with positive immunoglobulin E and skin prick testing; eye findings such as cataracts; and excessive skin reactivity to touching foods, pressure and environmental triggers. These major and minor criteria actually have been staring us in the face for almost 40 years with the concept of comorbidities being part and parcel of the definition of atopic dermatitis and the atopic diathesis.

Recently, both pediatric psoriasis and atopic dermatitis have been linked to cutaneous infections and psychosocial disorders such as anxiety, depression and hyperactivity for the children involved and their parents. Linkage to cutaneous autoimmunity, including vitiligo and alopecia areata, may be noted in both sets of diseases.

The most important and well-described series of comorbidities shared by these two diseases is the association with obesity and the metabolic syndrome—a cluster of conditions characterized by increased risk of heart disease, stroke and diabetes. Early childhood obesity has been associated with atopic dermatitis development and severity. In psoriasis, increased abdominal girth and obesity may precede disease by a few years, suggesting their role as triggers in disease. One interesting feature of psoriatic disease is promising data from adults who had weight loss surgery and experienced psoriatic disease improvement.

Despite many common comorbidities, paediatric atopic dermatitis and paediatric psoriasis have many distinctive features.

In atopic dermatitis, the skin barrier is both weak and weakened by inflammation, allowing a series of unusual allergic features, i.e., the atopic march and infectious complications. Alternatively, in psoriasis the skin is triggered to thicken, and the joints may become inflamed.

Further divergence is seen in the clinical manifestations. In psoriasis, arthritis is the leading comorbidity, sometimes triggered by streptococcal disease. There also is a far more definitive association with metabolic syndrome features such as hypertension, hyperlipidemia and insulin resistance. Despite the common nature of psoriasis and the frequency of disease, atopic dermatitis has developed a more extensive laundry list of comorbidities, including infantile seborrheic dermatitis, *Malassezia* sensitization, dust allergy, asthma, food allergy, environmental allergens, contact dermatitis (e.g., lanolin, fragrance), prurigo, sleep disturbance, upper respiratory infections, warts, coxsackie generalization (e.g., eczema coxsackium) and cataracts.

At any rate, the development of screening tools and effective pharmacological interventions for patients of any age with inflammatory skin disease such as psoriasis or atopic dermatitis is a work in progress and it has become a crucial need nowadays. In this sense, the present invention provides for the use of conditioned media in which MSCs (mesenchymal stem cells) derived from a mammal pertaining to the genus *canis* are cultured in order to obtain such conditioned media suitable for the treatment of skin inflammatory disorders such as psoriasis or atopic dermatitis. It is particularly important to highlight, that the composition disclosed in the present invention is particularly effective in the xenogeneic treatment of human atopic dermatitis even though there is a high phylogenetic divergence between humans and dogs (see FIGS. 7 to 9).

In this regard, WO2008155659 discloses compositions for preventing or treating skin defects comprising conditioned cell medium from mesenchymal stem cells (MSC). In addition, this document indicates that MSCs can be obtained from humans, pigs, dogs, cats, mice, horses and other mammals. However, this document fails to specifically refer to "atopic dermatitis" or "psoriasis" and much less that these diseases can be treated with compositions comprising a conditioned cell medium from mesenchymal stem cells (MSC) obtained from dogs. In this sense, example 2 of the present invention indicates that MSCs from different origins provide different conditioned media under a qualitative and quantitative point of view. In fact, as illustrated in the figures (FIG. 2 in comparison to FIGS. 1, 3 and 4), a conditioned culture media from dog adipose MSCs is considerably different from a conditioned culture media obtained from human, cat or horse adipose tissue. Again, WO2008155659 provides no indication that a conditioned culture media specifically obtained from dog adipose MSCs is particularly useful for an effective treatment of dermatitis such as atopic dermatitis and psoriaris in human beings.

In addition, the fact that the present invention is preferably focus in the xenogeneic treatment of human atopic dermatitis, is certainly counterintuitive in light of documents such as WO2017041133 wherein the following statements can be found: "Adipose tissue may be human adipose tissue or mammalian animal adipose tissue, such as canine, equine or feline. Typically the source of the adipose tissue will be of the same species as the intended recipient of the MSCs . . . ."

Furthermore, although Mohd Matin Ansari "Therapeutic potential of canine bone marrow derived mesenchymal stem cells and its conditioned media in diabetic rat wound healing", Journal of stem cell research & therapy, vol. 3, no. 3, 1 Jan. 2013 (2014 Jan. 1), XP055406815, discloses the potential effectiveness of canine cells or its conditioned media in the treatment of wounds in different species such as in diabetic rats, such wounds are made by making a full thickness excision in the skin of the rat. On the contrary, skin inflammation causing atopic dermatitis rash is considered a type of allergic response. Therefore, the treatment of wounds generated in Mohd Matin Ansari et al and the treatment of atopic dermatitis are completely unrelated.

Finally, WO2017144552 is explicitly directed to compositions that mandatorily comprise dimethyl sulfoxide (DMSO), in fact DMSO is an essential feature in WO2017144552 since it enhances the treatment of the diseases detailed therein. However, WO2017144552 is not directed to the xenogeneic treatment of human atopic dermatitis or psoriaris, particularly in the context of a DMSO free composition, by using conditioned cell culture mediums obtained or obtainable by a process which comprises culturing a population of mesenchymal stromal cells (MSCs), wherein at least 50% of said population by number of cells are MSCs obtained from a mammal pertaining to the genus *canis*.

Therefore, the present invention is, as far as we know, the first to provide a composition comprising a conditioned cell culture medium obtained or obtainable by a process which comprises culturing a population of mesenchymal stromal cells (MSCs), wherein at least 50% of said population by number of cells are MSCs obtained from a mammal pertaining to the genus *canis*, for use in the xenogeneic treatment of human atopic dermatitis.

BRIEF DESCRIPTION OF THE INVENTION

According to the invention, instead of using stem cells, injured or lost tissues may be regenerated or repaired through enhancement of endogenous tissue repair by applying secretions from MSCs instead of, or in addition to, MSCs themselves. Specifically, we provide for the use of conditioned media in which the MSCs derived from a mammal pertaining to the genus *canis* are cultured in order to obtain such conditioned media suitable for the treatment of skin inflammatory disorders such as psoriasis or atopic dermatitis.

In particular, in table II (see description) we show a qualitative and quantitative comparison of the polypeptides secreted by MSCs from a mammal pertaining to the genus *canis* and those secreted from other mammals such as MSCs from cats or humans. In addition, the examples disclosed in the present specification clearly show a therapeutic effect linked to the use of the conditioned media obtained from culturing MSCs derived from a mammal pertaining to the genus *canis*, in particular a therapeutic effect linked to the treatment of atopic dermatitis or psoriasis.

With this approach, the present confounding issues associated with cell based therapy i.e. immune compatibility, tumorigenicity, xenozootic infections, costs, and waiting time if autologous cell preparations are used will be eliminated. Such an approach could potentially provide for the development of "off-the-shelf" MSC-based therapeutics at affordable costs and with better quality control and consistency.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855; and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

Thus a first aspect of the invention refers to a composition comprising a conditioned cell culture medium obtained or obtainable by a process which comprises culturing a population of mesenchymal stromal cells (MSCs), in which at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%, of said population by number of cells are MSCs obtained from a mammal pertaining to the genus *canis* or immortalized mesenchymal stromal cells obtained therefrom, in a nutrient rich liquid prepared for cell culture, preferably a basal media, such as DMEM, MEM, RPMI, or HAM'S with or without supplements such as serum containing media, serum free media, protein free media and chemically defined media; and collecting the conditioned cell culture medium,
wherein preferably the nutrient rich liquid is an animal and human serum-free media designed to grow MSCs, and
wherein preferably said composition does not comprise dimethyl sulfoxide (DMSO), for use in therapy.

It is preferably noted, that preferably the composition of the first aspect of the invention as a whole does not comprise human and animal serum components.

In a preferred embodiment of the first aspect of the invention or of any of its preferred embodiments, the MSCs are obtained from a mammal pertaining to the dog species.

In another preferred embodiment of the first aspect of the invention or of any of its preferred embodiments, the mesenchymal stromal cells are umbilical-cord derived stromal cells, adipose tissue-derived stromal cells, expanded mesenchymal stromal cells, expanded adipose tissue-derived stromal cells, bone-marrow derived stromal cells, expanded bone-marrow derived stromal cells or immortalized mesenchymal stromal cells obtained from any of the afore mentioned sources.

In another preferred embodiment of the first aspect of the invention or of any of its preferred embodiments, the nutrient rich liquid prepared for cell culture is a buffered saline solution comprising amino acids and vitamins supplemented with sodium pyruvate and glutamine. Preferably, the nutrient rich liquid prepared for cell culture is the basal media DMEM, MEM, RPMI, or HAM'S with or without supplements such as serum containing media, serum free media, protein free media and chemically defined media.

In a second aspect of the invention, the medical composition of the first aspect of the invention is used in the treatment or prevention of dermatitis in a human or animal subject. Preferably, said dermatitis is selected from the list consisting of atopic dermatitis, eczema and psoriasis. More preferably, the medical composition of the first aspect of the invention is use in the xenogeneic treatment of atopic dermatitis, eczema and/or psoriasis in a human subject.

A third aspect of the invention refers to the medical composition of the first aspect of the invention or to the composition for use according to the second aspect of the invention, wherein such composition is configurable to deliver the required amount of conditioned medium at the appropriate interval, in order to achieve optimal treatment.

In a preferred embodiment of the third aspect of the invention, such composition comprises excipients. Preferred excipients are those suitable for being included in topical compositions (i.e. dermatological acceptable excipient). The following auxiliary agents mentioned below can independent of each other be present in such composition: gelling agents, oils, waxes, thickening agents, hydrophilic or hydrophobic polymers, emulsifying agents, emollients, fatty acids, organic solvents, antioxidants, stabilizers, sequestering agents, acidifying or basifying agents, emulsifiers, emollients, surfactants, film formers, biological additives to enhance performance and/or consumer appeal such as amino acids, proteins, vanilla, aloe extract or bioflavinoids, buffering agents, chelating agents such as ethylenediaminetetraacetic acid (EDTA) or oxalic acid, colorants, dyes, propellants, antifoaming agents, wetting agents, vitamins, emulsion stabilizers, pH adjusters, thickening agents, fragrances, preservatives, opacifying agents, water and/or alcohols. The aforementioned auxiliary agents for the composition are used in the usual amounts known by those skilled in the art. Suitable oils for the compositions are selected from animal or vegetable or synthetic oils. Particularly preferred oils are selected from the group comprising liquid petrolatum, liquid paraffin, volatile and non-volatile silicone oils, isoparaffins, polyalphaolefins, fluorated and perfluorated oils. Suitable stabilizers for the compositions of the invention can be of non-ionic, anionic, cationic and amphiphilic nature. Preferred stabilizers are selected from the group comprising polyethylenglycol (PEG) and derivatives thereof, tweens, tritons, spans, polygycerines, polyalkyl glycerides, alkyl sulfonates, aryl sulfonates, alkyl phosphates, derivatives of alkyl-betaine and phosphatidylglycerole.

In another preferred embodiment of the third aspect of the invention, the composition is suitable for administering to a subject, preferably to a human subject, by any of the following routes of administration: intravenous, oral and topical. In a preferred embodiment of the third aspect of the invention the composition of the invention is a topical formulation that may be formulated in liquid or in semi-solid form, preferably as liquid, fluid, foam, cream, gel, paste, balsam, spray, ointment, lotion, conditioner, tonic, milk, mousse, emulsion, serum, oil, stick, shampoo, jelly, suspension, dispersion, lacquer, paint, elixir, drop or aerosol. In a particular embodiment, the active compounds of the invention were administered topically in a liposomal preparation.

DETAILED DESCRIPTION OF THE INVENTION

Definitions

Figure 1:
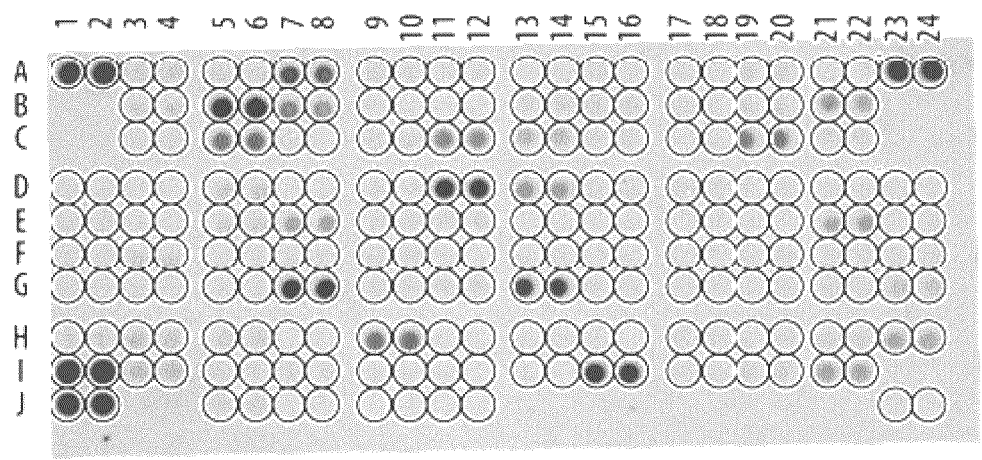
FIG. 1. Representative image of a Human XL Cytokine Array coordinates, hybridated with conditioned cultured media from human adipose derived mesenchymal stem cells.
Figure 1:
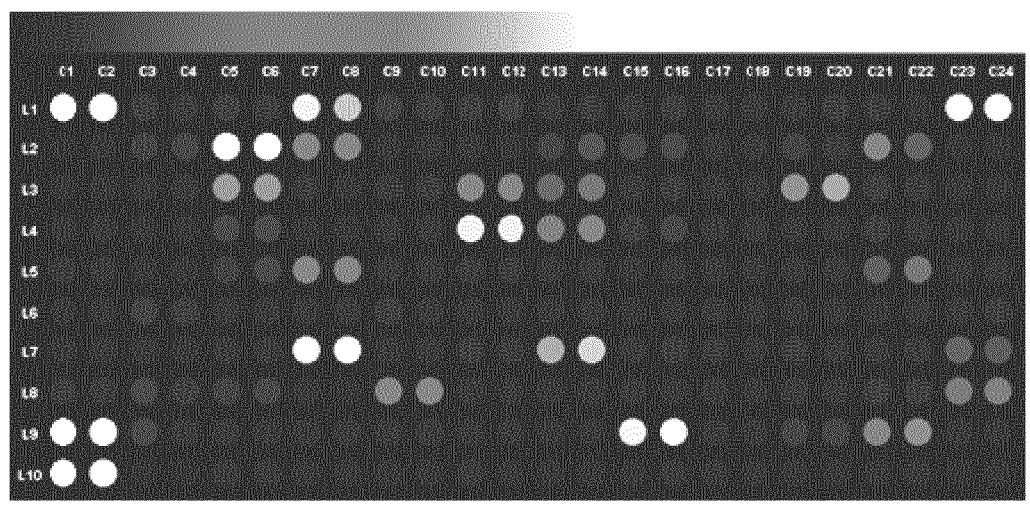

As used herein, the following terms and phrases shall have the meanings set forth below. Unless defined otherwise, all technical and scientific terms used herein have the same meaning as commonly understood to one of ordinary skill in the art to which this invention belongs.

The articles "a" and "an" refer to one or to more than one (i.e., to at least one) of the grammatical object of the article. By way of example, "an element" means one element or more than one element.

The term "about" when used in relation to a value relates to the value±10%.

By "adipose tissue" is meant any fat tissue. The adipose tissue may be brown or white adipose tissue, derived from, for example, subcutaneous, omental/visceral, mammary, gonadal, or other adipose tissue site. Preferably, the adipose tissue is subcutaneous white adipose tissue. The adipose tissue may comprise a primary cell culture or an immortalized cell line. The adipose tissue may be from any organism having fat tissue. In some embodiments, the adipose tissue is mammalian, and in further embodiments the adipose tissue is human. A convenient source of adipose tissue is liposuction surgery. However, it will be understood that neither the source of adipose tissue nor the method of isolation of adipose tissue is critical to the invention. If cells as described herein are desired for autologous transplantation into a subject, the adipose tissue will be isolated from that subject.

"Adipose tissue-derived stromal cells (ASCs)" refers to MSCs that originate from adipose tissue, generally from human adipose tissue (hASCs). These cells have been used in the present invention to reproduce the invention.

The term "cells/kg" as used herein shall be taken to mean the number of cells (e.g. MSC) administered per kilogram of patient body weight.

The term "culture" refers to the growth of cells, organisms, multicellular entities, or tissue in a medium. The term "culturing" refers to any method of achieving such growth, and may comprise multiple steps. The term "further culturing" refers to culturing a cell, organism, multicellular entity, or tissue to a certain stage of growth, then using another culturing method to bring said cell, organism, multicellular entity, or tissue to another stage of growth. A "cell culture" refers to a growth of cells in vitro. In such a culture, the cells proliferate, but they do not organize into tissue per se. A "tissue culture" refers to the maintenance or growth of tissue, e.g., explants of organ primordial or of an adult organ in vitro so as to preserve its architecture and function. A "monolayer culture" refers to a culture in which cells multiply in a suitable medium while mainly attached to each other and to a substrate. Furthermore, a "suspension culture" refers to a culture in which cells multiply while suspended in a suitable medium. Likewise, a "continuous flow culture" refers to the cultivation of cells or explants in a continuous flow of fresh medium to maintain cell growth, e.g. viability. The term "conditioned media" refers to the supernatant, e.g. free of the cultured cells/tissue, resulting after a period of time in contact with the cultured cells such that the media has been altered to include certain paracrine and/or autocrine factors produced by the cells and secreted into the culture. A "confluent culture" is a cell culture in which all the cells are in contact and thus the entire surface of the culture vessel is covered, and implies that the cells have also reached their maximum density, though confluence does not necessarily mean that division will cease or that the population will not increase in size.

The term "culture medium" or "medium" is recognized in the art, and refers generally to any substance or preparation used for the cultivation of living cells. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatine and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. Similarly, a powder mixture that when mixed with water or other liquid becomes suitable for cell culture may be termed a "powdered medium". "Defined medium" refers to media that are made of chemically defined (usually purified) components. "Defined media" do not contain poorly characterized biological extracts such as yeast extract and beef broth. "Rich medium" includes media that are designed to support growth of most or all viable forms of a particular species. Rich media often include complex biological extracts. The term "basal medium" refers to a medium which promotes the growth of many types of microorganisms which do not require any special nutrient supplements. Most basal media generally comprise four basic chemical groups: amino acids, carbohydrates, inorganic salts, and vitamins. A basal medium generally serves as the basis for a more complex medium, to which supplements such as serum, buffers, growth factors, lipids, and the like are added. Examples of basal media include, but are not limited to, Eagles Basal Medium, Minimum Essential Medium, Dulbecco's Modified Eagle's Medium, Medium 199, Nutrient Mixtures Ham's F-10 and Ham's F-12, McCoy's 5 A, Dulbecco's MEM/F-I 2, RPMI 1640, and Iscove's Modified Dulbecco's Medium. It is noted that many modifications of Eagle's Medium have been developed since the original formulation appeared in the literature. Among the most widely used of these modifications is Dulbecco's Modified Eagle's medium (DMEM). DMEM is a modification of Basal Medium Eagle (BME) that contains a four-fold higher concentration of amino acids and vitamins, as well as additional supplementary components. The original DMEM formula contains 1000 mg/L of glucose and was first reported for culturing embryonic mouse cells (low glucose DMEM). A further alteration with 4500 mg/L glucose has proved to be optimal for cultivation of certain cell types (high glucose DMEM). DMEM is a preferred basal media in the context of the present invention. It is noted that the basal media referred to in the present invention is an animal/human serum-free media or a chemically defined serum-free and xeno free media designed to grow MSCs such as Eagles Basal Medium or Dulbecco's Modified Eagle's Medium (DMEM).

In the context of the present invention, an animal and human serum-free media is understood as a media that contains no animal or human-derived blood or serum components. In particular, it refers to a media that contains no human or animal proteins present in the blood of humans or animals such as albumin or fetal bovine serum or fetal calf serum (that is to say, the medium contains no animal or human-derived blood or serum components). An example of an animal and human serum-free media is DMEM.

The terms "comprise" and "comprising" are used in the inclusive, open sense, meaning that additional elements may be included.

The term "expanded" as used herein when referring to cells shall be taken to have its usual meaning in the art, namely cells that have been proliferated in vitro. A MSC can be expanded to provide a population of cells that retain at least one biological function of the MSC, typically the ability to adhere to a plastic surface, under standard culture conditions. The expanded population of cells may retain the ability to differentiate into one or more cell types.

The term "including" is used herein to mean "including but not limited to". "Including" and "including but not limited to" are used interchangeably.

"Mesenchymal stromal cells (also referred to herein as "MSCs") are multipotent stromal cells, i.e. they are cells which are capable of giving rise to multiple different types of cells. These types of cells are defined by their plastic adherent growth and subsequent expansion under specific culture conditions and by their in vitro and in vivo differentiation potential (Caplan A I: Mesenchymal Stem Cells. J Orthop Res 1991, 9:641-650; Zuk P A, Zhu M, Mizuno H, Huang J, Futrell J W, Katz A J, Benhaim A J, Lorenz H P, Hedrick M H: Multi-lineage cells from human adipose tissue: implication for cell-based therapies. Tissue Eng 2001, 7:211-228; Huang J I, Beanes S R, Zhu M, Lorenz H P, Hedrick M H, Benhaim P: Rat extramedullary adipose tissue as a source of osteochondrogenic progenitor cells. Plast Reconstr Surg 2002, 109:1033-1041; Dennis J E, Caplan A I: Differentiation potential of conditionally immortalized mesenchymal progenitor cells from adult marrow of a H-2 Kb-tsA58 transgenic mouse. J Cell Physiol 1996, 167(3):523-538; Johnstone B, Hering T M, Caplan A I, Goldberg V M, Yoo J U: In vitro chondrogenesis of bone marrow-derived mesenchymal progenitor cells. Exp Cell Res 1998, 238(1):265-272; Dennis J E, Merriam A, Awadallah A, Yoo J U, Johnstone B, Caplan A I: A quadr-icpotential mesenchymal progenitor cell isolated from the marrow of an adult mouse. J Bone Miner Res 1999, 14(5):700-709; Kopen G C, Prockop D J, Phinney D G: Marrow stromal cells migrate throughout forebrain and cerebellum, and they differentiate into astrocytes after injection into neonatal mouse brains. Proc Natl Acad Sci USA 1999, 96:10711-10716; Toma C, Pittenger M F, Cahill K S, Byrne B J, Kessler P D: Human mesenchymal stem cells differentiate to a cardiomyocyte phenotype in the adult murine heart. Circulation 2002, 105:93-98). MSCs are well known in the literature as shown above and as such form part of the common general knowledge attributable to the skilled person in the art.

MSCs have been isolated from numerous mammals in order to practice the present invention. For example, MSCs have been derived from various equine tissues, including bone marrow (Arnhold S J, Goletz I, Klein H, Stumpf G, Beluche L A, Rohde C, Addicks K, Litzke L F. Isolation and characterization of bone marrow-derived equine mesenchymal stem cells. Am J Vet Res 2007, 68, 1095-1105; Kisiday J D, Kopesky P W, Evans C H, Grodzinsky A J, Mcllwraith C W, Frisbie D D. Evaluation of adult equine bone marrow- and adipose-derived progenitor cell chondrogenesis in hydrogel cultures. J Orthop Res 2008, 26, 322-33; Smith R K W, Korda M, Blunn G W, Goodship A E. Isolation and implantation of autologous equine mesenchymal stem cells from bone marrow into the superficial digital flexor tendon as a potential novel treatment. Equine Vet J 2003, 35, 99-102), adipose tissue (Vidal M A, Kilroy G E, Johnson J R, Lopez M J, Moore R M, Gimble J M. Cell growth characteristics and differentiation frequency of adherent equine bone marrow-derived mesenchymal stromal cells: adipogenic and osteogenic capacity. Vet Surg 2006, 35, 601-610.), peripheral blood, umbilical cord blood, umbilical cord matrix, and amniotic fluid. However, it is noted that the present invention is directed to the use of canine MSCs, in particular isolated from bone marrow and adipose tissue. Such canine MSCs are well documented in Hiroshi Takemitsu et al. Comparison of bone marrow and adipose tissue-derived canine mesenchymal stem cells. BMC Veterinary Research 2012, 8:150. Lastly, MSCs have been successfully isolated from bone marrow and adipose tissue (Caplan A I: Mesenchymal Stem Cells. J Orthop Res 1991, 9:641-650. Zuk P A, Zhu M, Mizuno H, Huang J, Futrell J W, Katz A J, Benhaim A J, Lorenz H P, Hedrick M H: Multi-lineage cells from human adipose tissue: implication for cell-based therapies. Tissue Eng 2001, 7:211-228. Huang J I, Beanes S R, Zhu M, Lorenz H P, Hedrick M H, Benhaim P: Rat extramedullary adipose tissue as a source of osteochondrogenic progenitor cells. Plast Reconstr Surg 2002, 109:1033-1041.) in humans.

A "patient", "subject" or "host" to be treated by the subject method may mean either a human or non-human animal.

The term "pharmaceutical composition" refers to a composition intended for use in therapy, no matter if it is for human or animal therapy, so that within the term pharmaceutical composition of the present invention veterinary compositions are encompassed. The compositions of the invention are pharmaceutical compositions, intended for use in the treatment of a patient or host.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

As used herein, the term "solution" includes a pharmaceutically acceptable carrier or diluent in which the MSCs used in the invention remain viable.

The term "substantially pure", with respect to MSC populations, refers to a population of cells in which at least about 50%, 60%, 70%, 75%, at least about 85%, at least about 90%, or at least about 95%, by number of the cells are MSCs. In other words, the term "substantially pure", with respect to MSC populations, refers to a population of cells that contains less than about 50%, less than about 30%, less than about 20%, less than about 10%, or less than about 5%, by number of lineage committed cells. "Support" as used herein refers to any device or material that may serve as a foundation or matrix for the growth of adipose tissue-derived stromal cells.

DESCRIPTION

A first aspect of the invention refers to a composition comprising a conditioned cell culture medium obtained or obtainable by a process which comprises culturing a population of mesenchymal stromal cells (MSCs), in which at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%, of said population by number of cells are MSCs obtained from a mammal pertaining to the genus *canis*, in a nutrient rich liquid prepared for cell culture, preferably a basal media; and collecting the conditioned cell culture medium, wherein preferably the nutrient rich liquid is an animal and human serum-free media designed to grow MSCs, and wherein said composition preferably does not comprise dimethyl sulfoxide (DMSO), for use in therapy.

The MSCs of the first aspect of the invention are undifferentiated stromal cells having the capacity to differentiate to other cells, and are typically derived from connective tissue, and are thus non-hematopoietic cells. The term "connective tissue" refers to tissue derived from mesenchyme and includes several tissues which are characterized in that their cells are included within the extracellular matrix. Among the different types of connective tissues, adipose and cartilaginous tissues are included. In one embodiment, the MSCs are from the stromal fraction of the adipose tissue. In another embodiment, the MSCs are obtained from chondrocytes e.g. from hyaline cartilage. In another embodiment, the MSCs are obtained from skin. Also, in another embodiment, the MSCs are obtained from bone marrow. Alternative sources of MSCs include but are not limited to periosteum, dental pulp, spleen, pancreas, ligament, tendon, skeletal muscle, umbilical cord and placenta. Other sources are induced pluripotent stem cells or embryonic stem cells.

It is important to note that the MSCs used to obtain the composition of the first aspect of the invention are obtained from a mammal pertaining to the genus *canis*, in particular these cells are canine MSCs. Typically, the canine MSCs are obtained from the stromal fraction of adipose tissue, i.e. they are canine adipose tissue-derived stromal cells (ASCs) or immortalized MSCs obtained therefrom. The canine MSCs are adherent to plastic under standard culture conditions. Canine MSCs are undifferentiated multipotent cells, having the capacity to differentiate into or towards somatic cells such as mesodermal cells (e.g. adipose, chondrocytes, osteoblasts) and optionally into or towards endodermal and/or ectodermal cell types or lineages. Typically, the cells have the capacity to differentiate into or towards at least two or all cell types selected from the group consisting of adipocytic, chondroblastic and osteoblastic lineages.

In one embodiment of the first aspect of the invention, the canine MSCs are in vitro culture expanded canine MSCs or the in vitro culture expanded progeny thereof (hereinafter both are referred to as expanded MSCs or "eMSCs"). Methods for the preparation of eMSCs are known in the art, for example as described in WO2007039150. eMSCs retain several phenotypic characteristics of MSC, e.g. the eMSCs are adherent to plastic under standard culture conditions and retain an undifferentiated phenotype.

eMSCs are undifferentiated multipotent cells, having the capacity to differentiate into somatic cells such as mesodermal cells. Whereas MSCs have the capacity to differentiate towards at least one or more specialized cell lineages such as but not limited to adipocyte, chondroblastic and osteoblastic lineages; typically in eMSCs this capacity to differentiate is reduced or may even be absent e.g. whereas a MSCs may differentiate towards at least the osteogenic and adipocytic lineages, the eMSCs derived therefrom may differentiate only towards the adipocytic lineage. This may be advantageous for therapeutic applications of the cells, where the cells may be administered to patients as it can reasonably be expected that unanticipated and potentially harmful differentiation of eMSCs will be less likely to occur.

In one embodiment the canine eMSCs may be the progeny of stem cells. Typically the canine eMSCs (i) do not express markers specific from APCs; (ii) do not express IDO constitutively (iii) do not significantly express MHC II constitutively. Typically expression of IDO or MHC II may be induced by stimulation with IFN-γ.

In addition, it is further noted that the cell population referred to in the first aspect of the invention is also referred to as "cell populations of the invention". Typically, the canine MSCs are expanded ASCs, typically allogeneic or autologous expanded ASCs. Typically, the cell populations of the invention are a homogenous or substantially homogenous population of canine MSCs and/or canine eMSCs. Cell populations of the invention comprise essentially canine MSCs and/or canine eMSCs, however cell populations of the invention may also comprise other cell types. Accordingly in one embodiment the invention provides cell populations of the invention in which at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%, of the cells are canine MSCs and/or canine eMSCs.

In one embodiment, the eMSCs are eASCs, for example human eASCs. In a particular embodiment, the cells are allogeneic with respect to the subject to be treated. In another particular embodiment, the cells are autologous with respect to the subject to be treated.

Typically, a cell population of the invention may have the capacity to differentiate towards at least one or more specialized cell lineages such as but not limited to adipocytic, chondroblastic and osteoblastic lineages. In one embodiment a cell population of the invention may have the capacity to differentiate into or towards at least two or all cell types selected from the group consisting of adipocytic, chondroblastic and osteoblastic lineages. However, in an alternative embodiment this capacity to differentiate is reduced or may even be absent e.g. whereas a MSC may differentiate towards at least the osteogenic and adipocytic lineages, the eMSC population derived therefrom may differentiate only towards the adipocytic lineage. This may be advantageous for therapeutic applications of the cells, where the cells may be administered to patients as it can reasonably be expected that unanticipated and potentially harmful differentiation of eMSCs will be less likely to occur.

As refer in the first aspect of the invention, and as exemplified in the examples, we provide a medium which is conditioned by culture of mesenchymal stem cells (MSCs) obtained from a mammal pertaining to the genus *canis*. Such a conditioned medium comprises molecules secreted by such MSCs, including unique gene products. Such a conditioned medium, and combinations of any of the molecules comprised therein, including in particular proteins or polypeptides, may be used in the treatment of a disease. They may be used to supplement the activity of, or in place of, the MSCs, for the purpose of for example treating or preventing a disease.

The conditioned medium of the first aspect of the invention may be made by culturing canine MSCs in a medium, such as a nutrient rich liquid prepared for cell culture, preferably a basal media; wherein the nutrient rich liquid is preferably an animal and human serum-free media designed to grow MSCs, for a predetermined length of time. The conditioned medium will thus comprise polypeptides secreted by the canine MSCs, as described in the Examples.

In a preferred embodiment, the serum-free media comprises Knockout DMEM media (Invitrogen-Gibco, Grand Island, N.Y.).

Notwithstanding the above, the conditioned media of the first aspect of the invention may be made by any media suitable for propagating canine MSCs and can thus have any of several different formulas, as long as the cells obtained have the desired characteristics, and can be propagated further. Suitable sources are as follows: Dulbecco's modified Eagles medium (DMEM), Gibco #I 1965-092; Knockout Dulbecco's modified Eagles medium (KO DMEM), Gibco #10829-018; 200 mM L-glutamine, Gibco #15039-027; non-essential amino acid solution, Gibco 11140-050; beta-mercaptoethanol, Sigma #M7522; human recombinant basic fibroblast growth factor (bFGF), Gibco #13256-029. Exemplary serum-containing embryonic stem (ES) medium is made with 80% DMEM (typically KO DMEM), 20% defined fetal bovine serum (FBS) not heat inactivated, 0.1 mM non-essential amino acids, 1 mM L-glutamine, and 0.1 mM beta-mercaptoethanol. The medium is filtered and stored at 4 degrees C. for no longer than 2 weeks. Serum-free embryonic stem (ES) medium is made with 80% KO DMEM, 20% serum replacement, 0.1 mM non-essential amino acids, 1 mM L-glutamine, and 0.1 mM beta-mercaptoethanol. An effective serum replacement is Gibco #10828-028. The medium is filtered and stored at 4 degrees C. for no longer than 2 weeks. Just before use, human bFGF is added to a final concentration of 4 ng/niL (Bodnar et al., Geron Corp, International Patent Publication WO 99/20741).

In a preferred embodiment, the media comprises Knockout DMEM media (Invitrogen-Gibco, Grand Island, N.Y.), supplemented with 10% serum replacement media (Invitrogen-Gibco, Grand Island, N.Y.), 5 ng/ml FGF2 (Invitrogen-Gibco, Grand Island, N.Y.) and 5 ng/ml PDGF AB (Peprotech, Rocky Hill, N.J.).

The conditions for culturing the canine MSCs in order to obtain the conditioned media of the present invention are clearly illustrated in example 1; however, these conditions can be optimized appropriately.

The conditioned medium of the present invention may be used in therapy as is, or after one or more treatment steps. For example, the conditioned medium may be UV treated, filter sterilised, etc. One or more purification steps may be employed.

In particular, the conditioned media may be concentrated, for example by dialysis or ultrafiltration. For example, the medium may be concentrated using membrane ultrafiltration with a nominal molecular weight limit (NMWL) of for example 3K.

We also provide for a composition comprising one or more, preferably all, of the polypeptides described in the Examples, in lieu of, or to supplement such a conditioned medium.

Conditioned media from mesenchymal stem cells such as those made according to the methods and compositions described here may be used for a variety of commercially important research, diagnostic, and therapeutic purposes.

The conditioned media from mesenchymal stem cells may in particular be used for the preparation of a pharmaceutical composition for the treatment of disease. Such disease may comprise a disease treatable by regenerative therapy, including skin disease, burns, psoriasis or atopic dermatitis. In this sense, it is herein noted that, as shown in the examples, analysis of the secreted proteins to the culture media by the canine MSCs (see table II) shows that the proteins expressed are involved in a number of biological processes including: tissue differentiation including vascularization, hematopoiesis and skeletal development. We therefore provide generally for the use of mesenchymal stem cells (MSCs) obtained from a mammal pertaining to the genus *canis* or medium conditioned by mesenchymal stem cells (MSCs) obtained from a mammal pertaining to the genus *canis*, in the regulation of any of these biological processes.

Furthermore, the mesenchymal stem cells (MSCs) obtained from a mammal pertaining to the genus *canis* may be used to treat diseases in which these biological processes may have a role in, or whose repair or treatment involves any one or more of these biological processes. Similarly, the proteins expressed by the mesenchymal stem cells (MSCs) obtained from a mammal pertaining to the genus *canis*, singly or in combination, preferably in the form of a conditioned medium, may be used to supplement the activity of, or in place of, the mesenchymal stem cells (MSCs) obtained from a mammal pertaining to the genus *canis*, for the purpose of for example treating or preventing such diseases.

Accordingly, such a conditioned medium may be used to treat a cutaneous wound, a dermatologic disorder, a dermatological lesion, dermatitis, psoriasis, condyloma, verruca, hemangioma, keloid, skin cancer, atopic dermatitis, Behcet disease, chronic granulomatous disease, cutaneous T cell lymphoma, and ulceration. In particular, such a conditioned medium may be used to treat psoriasis or atopic dermatitis.

In addition, the conditioned medium may be used to aid wound healing or scar reduction in an individual.

In particular, the conditioned medium may be used to regulate the processes involved in vascularisation, hematology (specifically immune processes) or musculoskeletal development, etc.

Preferably, said conditioned medium or a composition containing or comprising the same, does not comprise dimethyl sulfoxide (DMSO), and is used in the xenogeneic treatment of atopic dermatitis, eczema and/or psoriasis in a human subject.

Furthermore, any one or more proteins secreted from the MSCs described here, including in the form of conditioned media, may be used for the same purposes as the MSCs described herein. We therefore provide a composition comprising one or more, preferably substantially all, the polypeptides which are present in the conditioned medium. Specifically, we provide a composition comprising one or more, preferably substantially all, the polypeptides set out in table II, in particular of the case of MSCs derived from the adipose tissue of a dog.

Such a composition may be used for any purpose the conditioned medium may be used. Unless the context dictates otherwise, the term "conditioned medium" should be taken to include not only cell culture medium exposed to MSCs as well as such a composition comprising one or more, preferably substantially all, the polypeptides which are present in the conditioned medium (see table II).

It will be evident that the methods and compositions described here enable the production of conditioned media from mesenchymal stem cells. Thus, any uses of mesenchymal stem cells will equally attach to conditioned media from mesenchymal stem cells.

The conditioned medium as described in this document may be delivered to the human or animal body by any suitable means.

We therefore describe a pharmaceutical or cosmetic composition or delivery system for delivering a conditioned medium as described in this document to a target cell, tissue, organ, animal body or human body, and methods for using the pharmaceutical or cosmetic composition or delivery system to deliver conditioned medium to a target. The delivery system may comprise a source of conditioned medium, such as a container containing the conditioned medium. The delivery system may comprise a dispenser for dispensing the conditioned medium to a target.

Accordingly, we provide a delivery system for delivering a conditioned medium, comprising a source of conditioned medium as described in this document together with a dispenser operable to deliver the conditioned medium to a target.

We further provide for the use of such a delivery system in a method of delivering a conditioned medium to a target.

Delivery systems for delivering fluid into the body are known in the art, and include injection, surgical drips, cathethers (including perfusion cathethers) such as those described in U.S. Pat. No. 6,139,524, for example, drug delivery catheters such as those described in U.S. Pat. No. 7,122,019.

It will be evident that the particular delivery should be configurable to deliver the required amount of conditioned medium at the appropriate interval, in order to achieve optimal treatment. A preferred delivery or administration of the conditioned medium is the topical delivery or administration. For this purpose, the composition or delivery system may have excipients. An excipient as defined in present specification, is an inactive substance used as a carrier or vehicle for the conditioned medium comprised in the composition. The compositions of the invention may comprise any excipient, preferably suitable for being included in topical compositions (i.e. dermatological acceptable excipient). The following auxiliary agents mentioned below can independent of each other be present in the composition of the invention: gelling agents, oils, waxes, thickening agents, hydrophilic or hydrophobic polymers, emulsifying agents, emollients, fatty acids, organic solvents, antioxidants, stabilizers, sequestering agents, acidifying or basifying agents, emulsifiers, emollients, surfactants, film formers, biological additives to enhance performance and/or consumer appeal such as amino acids, proteins, vanilla, aloe extract or bioflavinoids, buffering agents, chelating agents such as ethylenediaminetetra-acetic acid (EDTA) or oxalic acid, colorants, dyes, propellants, antifoaming agents, wetting agents, vitamins, emulsion stabilizers, pH adjusters, thickening agents, fragrances, preservatives, opacifying agents, water and/or alcohols. The aforementioned auxiliary agents for the composition of the invention are used in the usual amounts known by those skilled in the art. Suitable oils for the compositions of the invention are selected from animal or vegetable or synthetic oils. Particularly preferred oils are selected from the group comprising liquid petrolatum, liquid paraffin, volatile and non-volatile silicone oils, isoparaffins, polyalphaolefins, fluorated and perfluorated oils. Suitable stabilizers for the compositions of the invention can be of non-ionic, anionic, cationic and amphiphilic nature. Preferred stabilizers are selected from the group comprising polyethylenglycol (PEG) and derivatives thereof, tweens, tritons, spans, polygycerines, polyalkyl glycerides, alkyl sulfonates, aryl sulfonates, alkyl phosphates, derivatives of alkyl-betaine and phosphatidylglycerole.

Emulsifiers may be used in the compositions of present invention in amounts effective to provide uniform blending of ingredients of said compositions. Suitable emulsifiers include anionics such as fatty acid soaps, e.g., potassium stearate, sodium stearate, ammonium stearate, and triethanolamine stearate; polyol fatty acid monoesters containing fatty acid soaps, e.g., glycerol monostearate containing either potassium or sodium salt; sulfuric esters (sodium salts), e.g., sodium lauryl 5 sulfate, and sodium acetyl sulfate; and polyol fatty acid monoesters containing sulfuric esters, e.g., glyceryl monostearate containing sodium lauryl surfate; (ii) cationics chloride such as N(stearoyl colamino formylmethyl) pyridium; N-soya-N-ethyl morpholinium ethosulfate; alkyl dimethyl benzyl ammonium chloride; diisobutylphenoxytheoxyethyl dimethyl benzyl ammonium chloride; and acetyl pyridium chloride; and (iii) nonionics such as polyoxy ethylene fatty alcohol ethers, e.g., monostearate; polyoxy ethylene lauryl alcohol; polyoxypropylene fatty alcohol ethers, e.g., propoxylated oleyl alcohol; polyoxyethylene fatty acid esters, e.g., polyoxyethylene stearate; polyoxyethylene sorbitan fatty acid esters, e.g., polyoxyethylene sorbitan monostearate; sorbitan fatty acid esters, e. g., sorbitan; polyoxyethylene glycol fatty acid esters, e.g., polyoxyethylene glycol monostearate; and polyol fatty acid esters, e.g., glyceryl monostearate and propylene glycol monostearate; and ethoxylated lanolin derivatives, e.g., ethoxylated lanolins, ethoxylated lanolin alcohols and/or ethoxylated cholesterol.

Emollients may be also used in the compositions of the invention in such amounts to prevent or relieve dryness. Suitable emollients include, without limitation hydrocarbon oils and waxes; silicone oils; triglyceride esters; acetoglyceride esters; ethoxylated glyceride; alkyl esters; alkenyl esters; fatty acids; fatty alcohols; fatty alcohol ethers; ether-esters; lanolin and derivatives; polyhydric alcohols (polyols) and polyether derivatives; polyhydric alcohol (polyol) esters; wax esters; beeswax derivatives; vegetable waxes; phospholipids; sterols; and/or amides.

Surfactants can further be used too in the compositions of present invention. Suitable surfactants are for example those surfactants generally grouped as cleansing agents, emulsifying agents, foam boosters, hydrotropes, solubilizing agents, suspending agents and non-surfactants, which facilitate the dispersion of solids in liquids.

Film formers which may be preferably used in the compositions of present invention should keep the composition smooth and even and are preferably, without limitation. Suitable film formers are selected from the group comprising acrylamide/sodium acrylate copolymer; ammonium acrylates copolymer; Balsam Peru; cellulose gum; ethylene/maleic anhydride copolymer; hydroxyethylcellulose; hydroxypropylcellulose; polyacrylamide; polyethylene; polyvinyl alcohol; pvm/MA copolymer (vinyl methyl ether/maleicanhydride copolymer); PVP (polyvinylpyrrolidone); maleic anhydride polymer, vinylpyrrolidon/hexadecene copolymer; acryliclacrylate copolymer and the like. PH adjusters may also be used in the compositions of present invention. These pH adjusters are preferably selected from: ammonium hydroxide, triethanolamine or citric acid.

Thickening agents used for the compositions of the invention preferably are selected from: candelilla, carnauba, and microcrystalline waxes, crosslinked acrylic-acid polymers, carbomer, methylhydroxyethylcellulose, hydroxypropylmethylcellulose or hydroxy ethylcellulose and polyethylene thickeners.

Examples of preferred organic solvents for the compositions of present invention include lower aliphatic alcohols and polyols.

Suitable antioxidants for the compositions used in present invention are preferably selected from the group comprising ascorbic acid (vitamin C), sodium-L-ascorbate, calcium-L-ascorbate, ascorbyl palmitate, butylhydroxyanisole, butylhydroxytoluene, calcium-disodium-EDTA, isoascorbic acid, lecitine, lactic acid, polyphosphate, tocopherol (vitamin E), like [alphaj-tocopherol, [gamma]-tocopherol, [delta]-tocopherol, propylgallate, octylgallate, dodecylgallate, sodium-isoascorbate, citric acid, sodium citrate, potassium citrate and tin-II-chloride. Gelling agents, which are preferably used in the compositions of the invention, can be natural or synthetic polymers. Natural polymers are preferably selected from: Agar-Agar, alginate, pectin, carbomer, carrageenan, casein, dextrine, gelatine, arabic gum, keratine, locust bean gum, xanthan gum and the like. Preferred synthetic polymers which can be used in the compositions of the invention are selected from: acylic acid polymers, polyacryl amides and alkylene oxide polymers.

As already indicated, any route of administration can be used for administering the compositions of the invention to the subject, being the preferred routes of administration intravenous, oral and topical. In a preferred embodiment the composition of the invention is a topical formulation that may be formulated in liquid or in semi-solid form, preferably as liquid, fluid, foam, cream, gel, paste, balsam, spray, ointment, lotion, conditioner, tonic, milk, mousse, emulsion, serum, oil, stick, shampoo, jelly, suspension, dispersion, lacquer, paint, elixir, drop or aerosol. In a particular embodiment, the active compounds of the invention were administered topically in a liposomal preparation. As used in the present invention, a "liposome" is an artificial vesicle that is composed of one or more concentric layers and is used especially to deliver substances (i.e. conditioned medium) to the body cells.

Topical administration of the composition of the invention leads to a high bioavailability of the active compounds of the conditioned medium. In pharmacology, bioavailability is used to describe the fraction of an administered dose of unchanged drug that reaches the systemic circulation, one of the principal pharmacokinetic properties of drugs. Therefore, the bioavailability is one of the essential tools in pharmacokinetics, and it must be considered when calculating dosages for non-intravenous routes of administration.

It will be evident that the delivery method will depend on the particular organ to which the conditioned medium is to be delivered, and the skilled person will be able to determine which means to employ accordingly.

The following examples are merely for illustrative purposes and do not limit the present invention.

EXAMPLES

Example 1. Obtention of the Conditioned Media of the Present Invention

In general terms the conditioned media of the present invention can be obtained by culturing MSCs (mesenchymal stem cells), preferably derived from dog adipose tissue, in a suitable cell media, preferably in DMEM supplemented with 10% FBS and PSG, until reaching a confluence of between 70% and 80%, such level of confluence is usually reached in passage 3.

The adipose tissue is obtained from one or several healthy donors. About 10-500 g of adipose tissue from each donor will produce one batch of master cell banks. The age of the donor may influence the in vitro lifespan of the cells, so the original donors will be under two years of age. The clinical history and the good general conditions of the donor will be assessed. Several samples will be collected to perform routine and disease tests and certify the absence of pathogens. The extraction of adipose tissue will be performed in an operation room or in a stable set up for the extraction according veterinarian surgeon's criteria. The tissue extraction will be performed by a qualified vet under animal welfare conditions.

The region for adipose tissue extraction will be preferably the hepatic falciform ligament, but adipose tissue can be also obtained from other intra-peritoneal fat or subcutaneous (ie. dock region). The procedure for adipose tissue collection will be as follows: Briefly, the zone will be thoroughly cleaned, shaved and disinfected according standard surgical techniques. Then, an incision is performed under local or systemic anaesthesia. The extracted adipose tissue is placed in a sterile recipient and processed accordingly.

Once such level of confluence is reached, the media is then discarded and the cells should be rinsed, preferably three times, with a saline solution such as PBS. Cells should be then cultured in a serum-free and antibiotic-free medium, such as DMEM, for at least about 24 hours. The conditioned media should be then collected and filtered through a 0.2-mm filter to remove cellular debris.

In particular, the conditioned media used in the present examples was obtained as follows:

Adipose tissue was obtained from dogs (*Canis lupus familiaris* L.), cats (*Felis silvestris catus* L.) and horses (*Equus caballus* L.) and also from humans, by aseptically collecting said tissues from the abdominal region of the animals and humans by surgical excision. MSCs obtained from such adipose tissue were then culture in DMEM supplemented with 10% FBS and PSG until reaching a confluence of between 70% and 80%, such level of confluence was reached in passage 3. The medium was then discarded and the cells were rinsed three times with PBS. Cells were then cultured with serum-free and antibiotic-free medium for periods of time ranging from 24 to 72 hours. The conditioned media was then collected and filtered through a 0.2-mm filter to remove cellular debris. It is noted that such 4 conditioned media (obtained from dogs, horses, humans and cats) was characterized as illustrated in example 2 below.

Cells were detached and characterized as MSC by means of surface markers identified by flow cytometry.

Example 2. Characterization of the Conditioned Media Obtained in Example 1

A Proteome Profiler Array was employed for the characterization of the conditioned media.

Human XL Cytokine Array Kit R&D Systems (Catalog Number ARY022B) was employed following manufacturer instructions. It is a rapid and sensitive tool to simultaneously detect cytokine differences between samples. This kit can use to measure the relative expression levels of up to 105 soluble human proteins.

In order to perform the characterization of the conditioned media, capture and control antibodies were spotted in duplicate on nitrocellulose membranes. Cell culture supernatants as obtained in example 1, were directly incubated overnight with the Proteome Profiler Human XL Cytokine Array. The membranes were washed to remove unbound material followed by incubation with a cocktail of biotinylated detection antibodies. Streptavidin-HRP and chemiluminescent detection reagents were then applied, and a signal was produced at each capture spot corresponding to the amount of protein bound.

Figure 2:
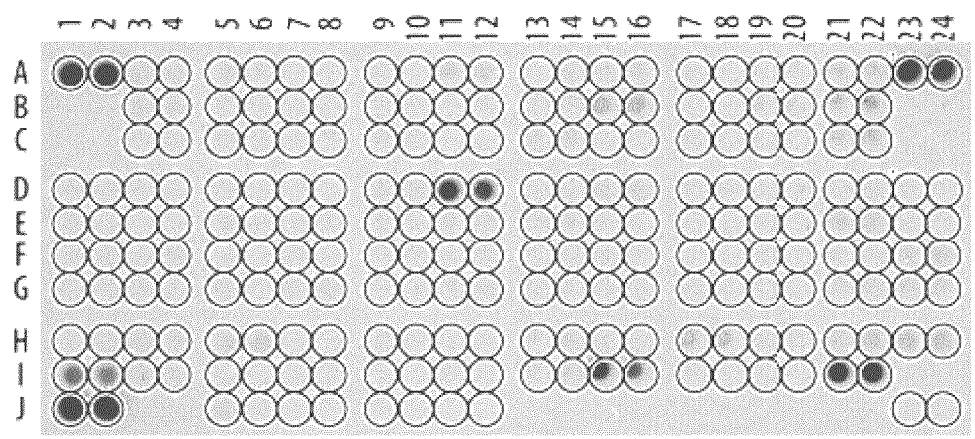
FIG. 2. Representative image of a Human XL Cytokine Array coordinates, hybridated with conditioned cultured media from dog adipose derived mesenchymal stem cells.
Figure 2:
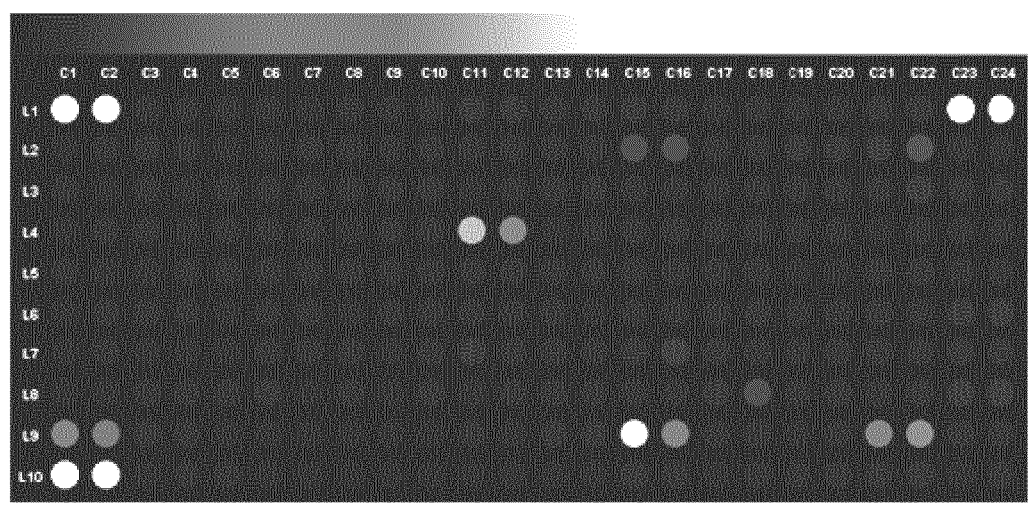
Figure 3:
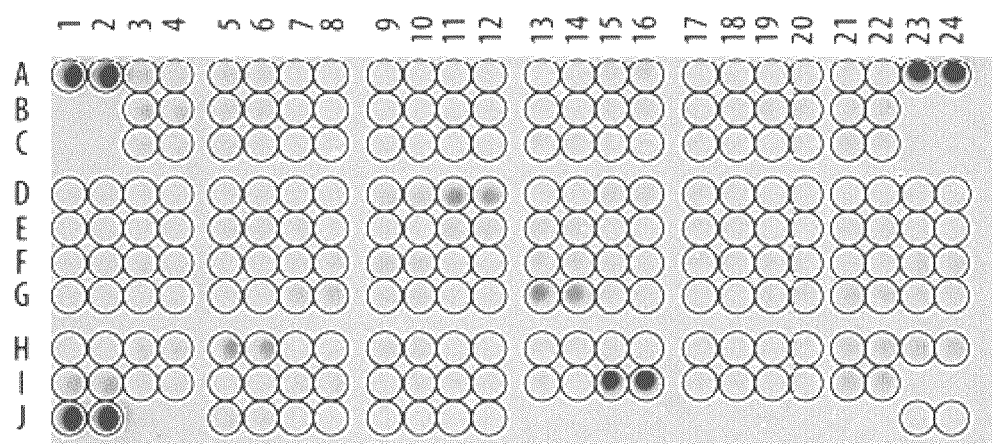
FIG. 3. Representative image of a Human XL Cytokine Array coordinates, hybridated with conditioned cultured media from cat adipose derived mesenchymal stem cells.
Figure 3:
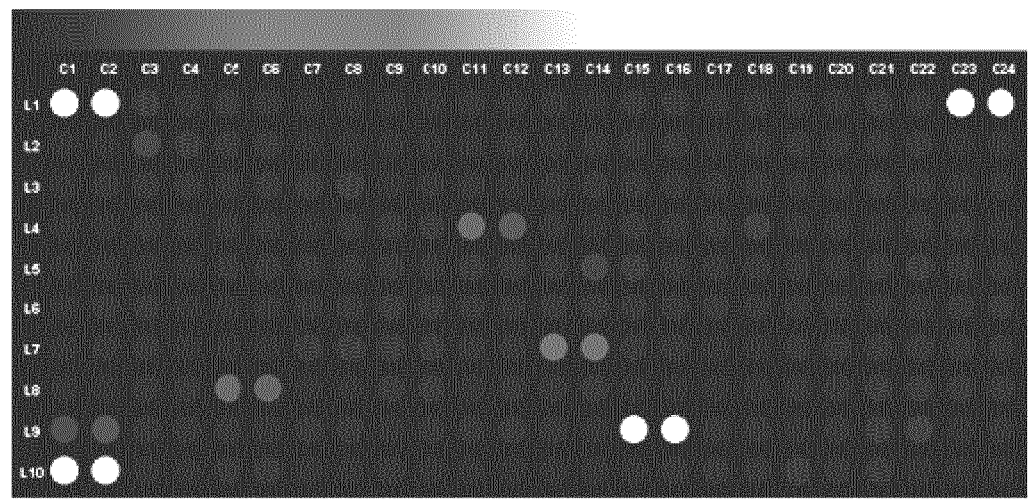
Figure 4:
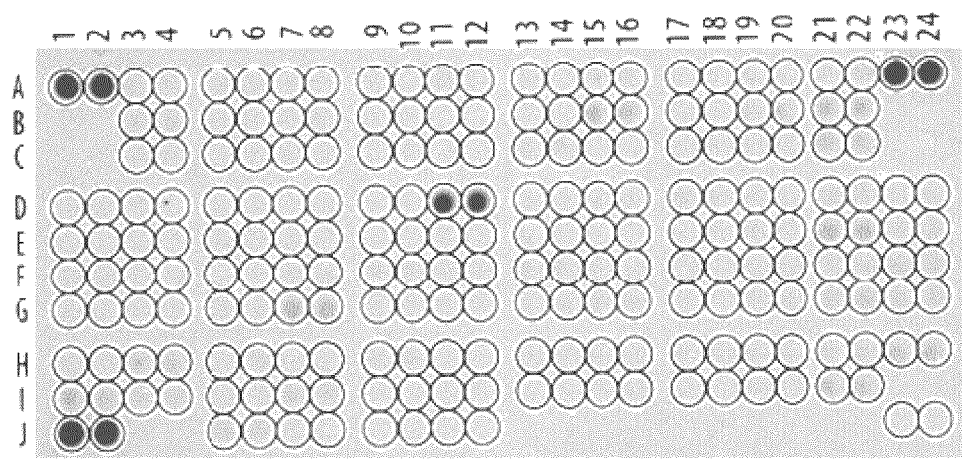
FIG. 4. Representative image of a Human XL Cytokine Array coordinates, hybridated with conditioned cultured media from horse adipose derived mesenchymal stem cells.
Figure 4:
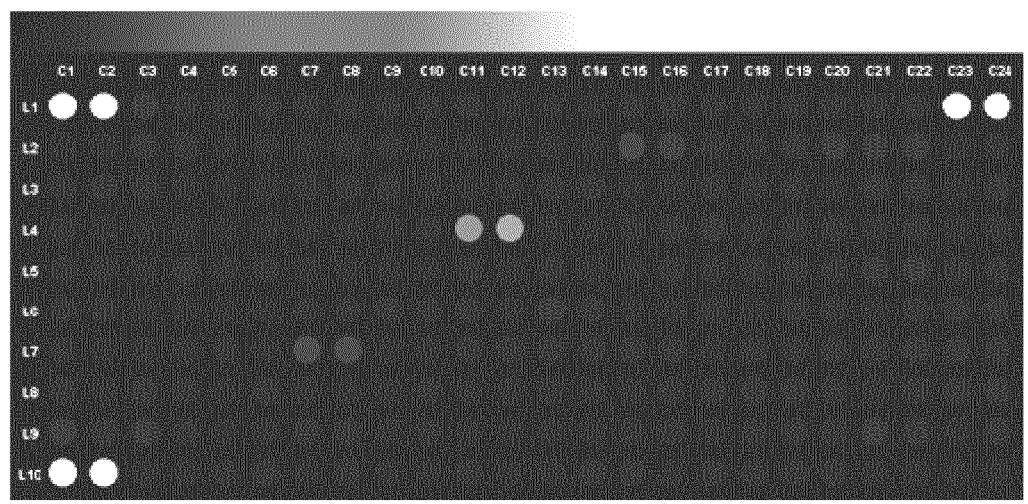

A list of the 105 different detected proteins are shown in Table I. Results for the four-different species can be found in the following figures: FIG. 1 (Human), FIG. 2 (Dog), FIG. 3 (Cat) and FIG. 4 (Horse).

TABLE I

Human XL Cytokine Array coordinates, showing positive and negative controls, the analytes checked, the Entrez gene ID of the analyte, and alternate nomenclature if exists.

| Coordinate | Analyte/Control | Entrez Gene ID | Alternate Nomenclature |
|---|---|---|---|
| A1, A2 | Reference Spots | N/A | RS |
| A3, A4 | Adiponectin | 9370 | Acrp30 |
| A5, A6 | Apolipoprotein A-I | 335 | ApoA1 |
| A7, A8 | Angiogenin | 283 | — |
| A9, A10 | Angiopoietin-1 | 284 | Ang-1, ANGPT1 |
| A11, A12 | Angiopoietin-2 | 285 | Ang-2, ANGPT2 |

TABLE I-continued

Human XL Cytokine Array coordinates, showing positive and negative controls, the analytes checked, the Entrez gene ID of the analyte, and alternate nomenclature if exists.

| Coordinate | Analyte/Control | Entrez Gene ID | Alternate Nomenclature |
|---|---|---|---|
| A13, A14 | BAFF | 10673 | BLyS, TNFSF13B |
| A15, A16 | BDNF | 627 | Brain-derived Neurotrophic Factor |
| A17, A18 | Complement | 727 | C5/C5a |
| A19, A20 | CD14 | 929 | — |
| A21, A22 | CD30 | 943 | TNFRSF8 |
| A23, A24 | Reference Spots | N/A | RS |
| B3, B4 | CD40 ligand | 959 | CD40L, TNFSF5, CD154, TRAP |
| B5, B6 | Chitinase 3-like 1 | 1116 | CHI3L1, YKL-40 |
| B7, B8 | Complement Factor D | 1675 | Adipsin, CFD |
| B9, B10 | C-Reactive Protein | 1401 | CRP |
| B11, B12 | Cripto-1 | 6997 | Teratocarcinoma-derived Growth |
| B13, B14 | Cystatin C | 1471 | CST3, ARMD11 |
| B15, B16 | Dkk-1 | 22943 | Dickkopf-1 |
| B17, B18 | DPPIV | 1803 | CD26, DPP4, Dipeptidyl-peptidase |
| B19, B20 | EGF | 1950 | Epidermal Growth Factor |
| B21, B22 | Emmprin | 682 | CD147, Basigin |
| C3, C4 | ENA-78 | 6374 | CXCL5 |
| C5, C6 | Endoglin | 2022 | CD105, ENG |
| C7, C8 | Fas Ligand | 356 | TNFSF6, CD178, CD95L |
| C9, C10 | FGF basic | 2247 | FGF-2 |
| C11, C12 | FGF-7 | 2252 | KGF |
| C13, C14 | FGF-19 | 9965 | — |
| C15, C16 | Flt-3 Ligand | 2323 | FLT3LG |
| C17, C18 | G-CSF | 1440 | CSF3 |
| C19, C20 | GDF-15 | 9518 | MIC-1 |
| C21, C22 | GM-CSF | 1437 | CSF2 |
| D1, D2 | GROα | 2919 | CXCL1, MSGA-a |
| D3, D4 | Growth Hormone | 2688 | GH, Somatotropin |
| D5, D6 | HGF | 3082 | Scatter Factor, SF |
| D7, D8 | ICAM-1 | 3383 | CD54 |
| D9, D10 | IFN-γ | 3458 | IFNG |
| D11, D12 | IGFBP-2 | 3485 | — |
| D13, D14 | IGFBP-3 | 3486 | — |
| D15, D16 | IL-1α | 3552 | IL-1F1 |
| D17, D18 | IL-1β | 3553 | IL-1F2 |
| D19, D20 | IL-1ra | 3557 | IL-1F3 |
| D21, D22 | IL-2 | 3558 | — |
| D23, D24 | IL-3 | 3562 | — |
| E1, E2 | IL-4 | 3565 | — |
| E3, E4 | IL-5 | 3567 | — |
| E5, E6 | IL-6 | 3569 | — |
| E7, E8 | IL-8 | 3576 | CXCL8 |
| E9, E10 | IL-10 | 3586 | — |
| E11, E12 | IL-11 | 3589 | — |
| E13, E14 | IL-12 p70 | 3593 | — |
| E15, E16 | IL-13 | 3596 | — |
| E17, E18 | IL-15 | 3600 | — |
| E19, E20 | IL-16 | 3603 | — |
| E21, E22 | IL-17A | 3605 | IL-17, CTLA8 |
| E23, E24 | IL-18 Bpa | 10068 | — |
| F1, F2 | IL-19 | 29949 | — |
| F3, F4 | IL-22 | 50616 | IL-TIF |
| F5, F6 | IL-23 | 51561 | IL-23A, SGRF |
| F7, F8 | IL-24 | 3627 | C49A, FISP, MDA-7, MOB-5, ST16 |
| F9, F10 | IL-27 | 246778 | — |
| F11, F12 | IL-31 | 386653 | — |
| F13, F14 | IL-32 | 9235 | — |
| F15, F16 | IL-33 | 90865 | C9orf26, DVS27, NF-HEV |
| F17, F18 | IL-34 | 146433 | C16orf77 |
| F19, F20 | IP-10 | 3627 | CXCL10 |
| F21, F22 | I-TAC | 6373 | CXCL11, SCYB9B |
| F23, F24 | Kallikrein 3 | 354 | PSA, KLK3 |
| G1, G2 | Leptin | 3952 | OB |
| G3, G4 | LIF | 3976 | — |
| G5, G6 | Lipocalin-2 | 3934 | NGAL, LCN2, Siderocalin |
| G7, G8 | MCP-1 | 6347 | CCL2, MCAF |
| G9, G10 | MCP-3 | 6354 | CCL7, MARC |
| G11, G12 | M-CSF | 1435 | CSF1 |
| G13, G14 | MIF | 4282 | — |
| G15, G16 | MIG | 4283 | CXCL9 |
| G17, G18 | MIP-1α/MIP-β | 6348/6351 | CCL3/CCL4 |
| G19, G20 | MIP-3α | 6364 | CCL20, Exodus-1, LARC |
| G21, G22 | MIP-3β | 6363 | CCL19, ELC |

TABLE I-continued

Human XL Cytokine Array coordinates, showing positive and negative controls, the analytes checked, the Entrez gene ID of the analyte, and alternate nomenclature if exists.

| Coordinate | Analyte/Control | Entrez Gene ID | Alternate Nomenclature |
|---|---|---|---|
| G23, G24 | MMP-9 | 4318 | CLG4B, Gelatinase B |
| H1, H2 | Myeloperoxidase | 4353 | MPO, Lactoperoxidase |
| H3, H4 | Osteopontin | 6696 | OPN |
| H5, H6 | PDGF-AA | 5154 | — |
| H7, H8 | PDGF-AB/BB | 5154/5155 | — |
| H9, H10 | Pentraxin 3 | 5806 | PTX3, TSG-14 |
| H11, H12 | PF4 | 5196 | CXCL4 |
| H13, H14 | RAGE | 177 | — |
| H15, H16 | RANTES | 6352 | CCL5 |
| H17, H18 | RBP-4 | 5950 | — |
| H19, H20 | Relaxin-2 | 6019 | RLN2, RLXH2 |
| H21, H22 | Resistin | 56729 | ADSF, FIZZ3, RETN |
| H23, H24 | SDF-1α | 6387 | CXCL12, PBSF |
| I1, I2 | Serpin E1 | 5054 | PAI-I, PAI-1, Nexin |
| I3, I4 | SHBG | 6462 | ABP |
| I5, I6 | ST2 | 9173 | IL-1 R4, IL1RL1, ST2L |
| I7, I8 | TARC | 6361 | CCL17 |
| I9, I10 | TFF3 | 7033 | ITF, TFI |
| I11, I12 | TfR | 7037 | CD71, TFR1, TFRC, TRFR |
| I13, I14 | TGF-α | 7039 | TGFA |
| I15, I16 | Thrombospondin-1 | 7057 | THBS1, TSP-1 |
| I17, I18 | TNF-α | 7124 | TNFSF1A |
| I19, I20 | uPAR | 5329 | PLAUR |
| I21, I22 | VEGF | 7422 | BEGFA |
| J1, J2 | Reference Spots | N/A | RS |
| J5, J6 | Vitamin D BP | 2638 | VDB, DBP, VDBP |
| J7, J8 | CD31 | 5175 | PECAM-1 |
| J9, J10 | TIM-3 | 84868 | HAVCR2 |
| J11, J12 | VCAM-1 | 7412 | CD106 |
| J23, J24 | Negative Controls | N/A | Control (−) |

Comparative results of the mean pixel density can be found in table II.

TABLE II

Mean pixel density of representative blots from the four analysed species.

| | | MEAN PIXEL DENSITY | | | |
|---|---|---|---|---|---|
| Coordinate | Analyte | Human | Dog | Cat | Horse |
| A7, A8 | Angiogenin | 16843 | 0 | 0 | 86 |
| B5, B6 | Chitinase 3-like 1 | 22816 | 0 | 521 | 13 |
| B7, B8 | Complement Factor | 11286 | 74 | 0 | 95 |
| B21, B22 | Emmprin | 6109 | 1775 | 431 | 1055 |
| C5, C6 | Endoglin | 13619 | 0 | 335 | 0 |
| C11, C12 | FGF-7 | 11032 | 0 | 20 | 0 |
| C13, C14 | FGF-19 | 5339 | 170 | 284 | 343 |
| C19, C20 | GDF-15 | 13684 | 142 | 133 | 78 |
| D11, D12 | IGFBP-2 | 17762 | 12412 | 3225 | 10783 |
| D13, D14 | IGFBP-3 | 8568 | 0 | 71 | 4 |
| E7, E8 | IL-8 | 8153 | 0 | 227 | 37 |
| E21, E22 | IL-17A | 4800 | 311 | 709 | 870 |
| G7, G8 | MCP-1 | 20066 | 37 | 768 | 2006 |
| G13, G14 | MIF | 15445 | 0 | 4358 | 159 |
| G23, G24 | MMP-9 | 3980 | 400 | 373 | 514 |
| H5, H6 | PDGF-AA | 1731 | 150 | 3482 | 65 |
| H9, H10 | Pentraxin 3 | 10306 | 8 | 555 | 85 |
| H23, H24 | SDF-1α | 6486 | 1146 | 609 | 629 |
| I1, I2 | Serpin E1 | 26138 | 6871 | 2264 | 837 |
| I15, I16 | Thrombospondin-1 | 18335 | 14541 | 17516 | 49 |
| I21, I22 | VEGF | 10296 | 10239 | 1095 | 941 |

In view of these results, it is thus clear that MSCs from different origins provide different conditioned media under a qualitative and quantitative view point.

The inventors of the present invention have surprisingly found that conditioned media obtained from dogs is particularly effective for the treatment of skin diseases such as atopic dermatitis and psoriasis not only in animals but also in human beings. The success in the xenogeneic use from dogs to humans, is not obvious. Moreover, the success is not obvious given the high phylogenetic divergence that exist between the two species.

Example 3. Clinical and Veterinary Results with the Composition of the Invention $1^{st}$ Case. Treatment of Atopic Dermatitis in a Dog An eight years old Pekingese with a cutaneous disease, an atopic dermatitis that caused a testicular affectation and a lot of itching was taken as a candidate for the treatment of the invention. In this individual, response to the usual corticosteroid prescription relapsed frequently. We treated such cutaneous disease employing the dog conditioned media as a cutaneal lotion over the wounds, spreading it two times a day during 6 weeks.

Figure 5:
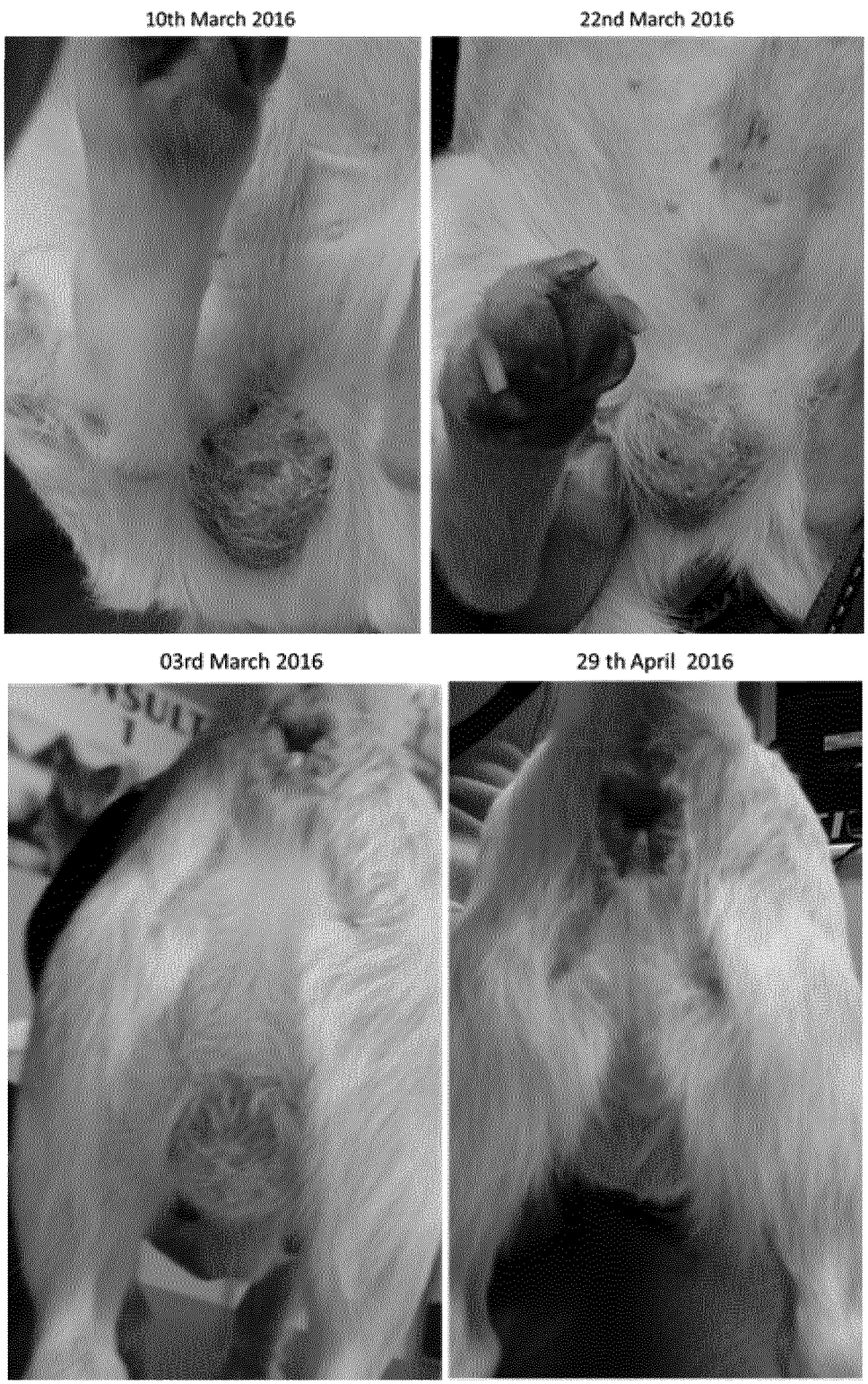
FIG. 5. Pekingnese dog treated with dog conditioned media. Images show the evolution of the wounds at four different points in time. Rush and skin peeling decreases during treatment up to complete remission in the $6^{th}$ week.

One and a half months after treatment with conditioned media, Pancho is in complete remission as illustrated in FIG. 5.

$2^{nd}$ Case. Treatment of a Siamese Cat Who Suffered from Severe Skin Burn Injuries.

Five years ago the Siamese cat subject was dropped into a frying pan of boiling oil. 30% of the body was affected, mainly legs and one of the flanks. Initial treatment consisted on silver sulfadiazid, ointment and liquid.

The cat recovered of the lesions during the first year, but a zone of approximately 10×5 cm was not recovered producing stable lesions over the last 3 years, with continuous exudate and itching.

Figure 6:
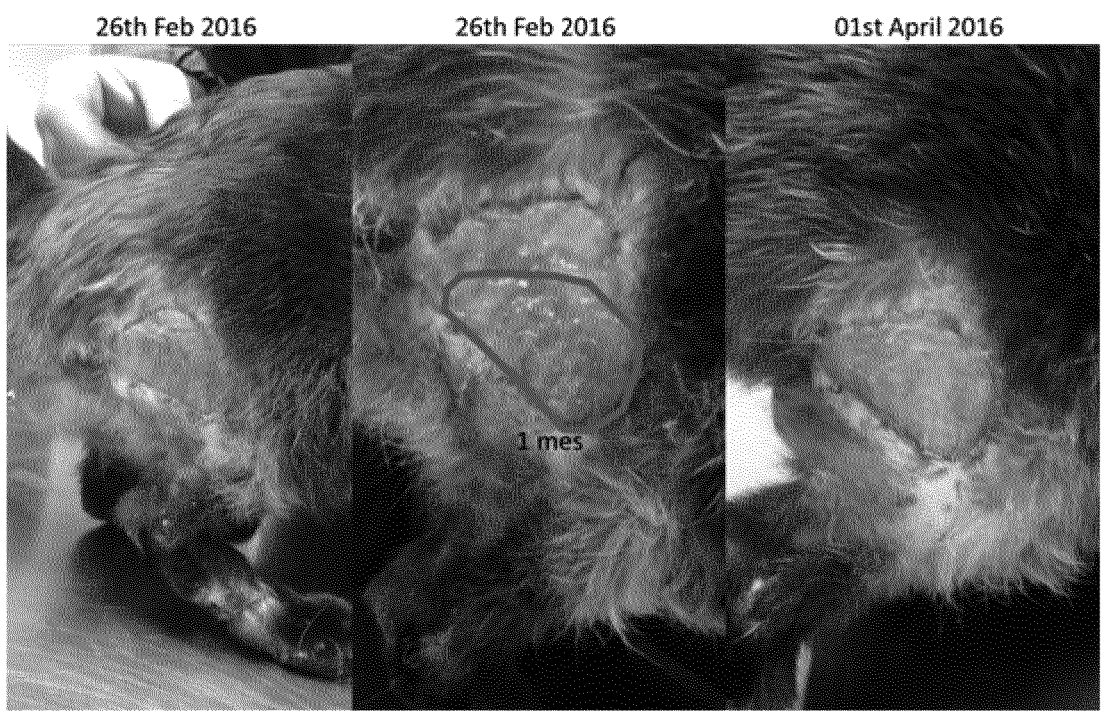
FIG. 6. Siamese cat treated with dog conditioned media. Images show the evolution of the wound at the beginning and the end of the treatment at week number 5. The size of the wound decreased as is shown in the comparative superposition.

We treated such stable lesions employing the dog conditioned media as a cutaneal lotion over the wound, spreading it two times a day during 6 weeks One and a half months after treatment with conditioned media, the size of the wound decreased as illustrated in FIG. 6.

3$^{rd}$ Case. Treatment of Psoriasis in a Human being

Male. 79 years old. Diagnosed of Psoriasis in 1975. The affected areas were the elbows and the right leg, where a large spot from the knee almost to the ankle could be clearly seen. For about eight or ten years small affected areas in hands.

The human subject suffered numerous treatments, including corticosteroid treatments.

We treated such stable lesions with dog conditioned media during 35 days, two times per day.

After employment of the conditioned culture, applied directly on the skin lesions in legs and hands employing a vaporizer, peeling and scales disappeared from the skin.

Figure 7:
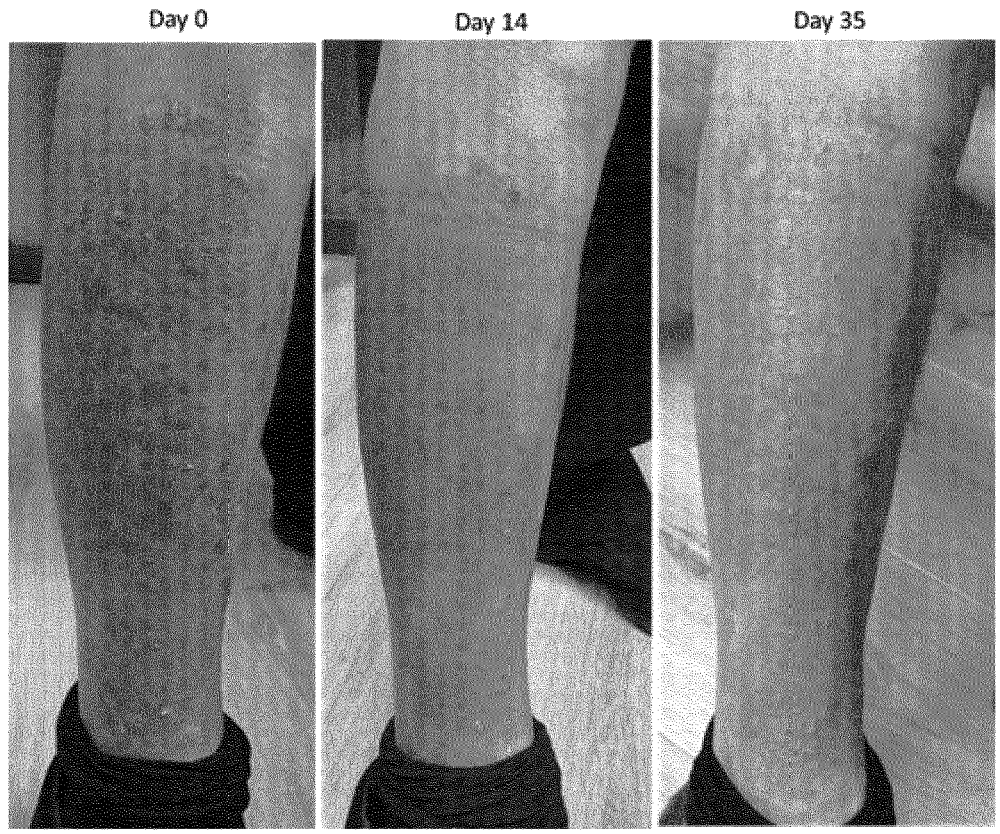
FIG. 7. 79 years old human male treated with dog conditioned media. Images show the evolution of the psoriatic wounds during the 35 days that last the treatment in leg and hands. Peeling and scales diminish notably from the skin.
Figure 7:
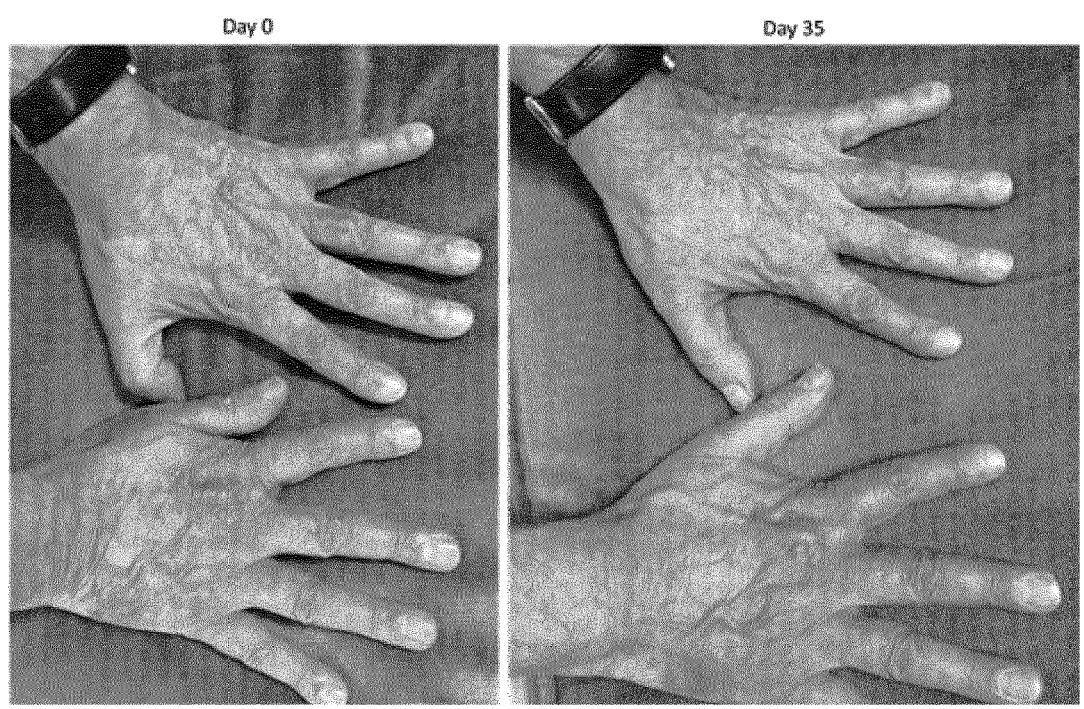

The small affected parts of the hands almost disappeared completely. Please refer to FIG. 7.

4$^{rd}$ Case. Treatment of Psoriasis in a Human Being

Female. 37 years old. Diagnosed of Psoriasis Arthritis for more than 10 years.

Treatment with salazopyrine (4 tablets/day). For acute crises, the treatment consisted of small doses of methotrexate. Such treatment was considered inefficient.

We treated the lesions produced by the psoriasis with dog conditioned media.

Figure 8:
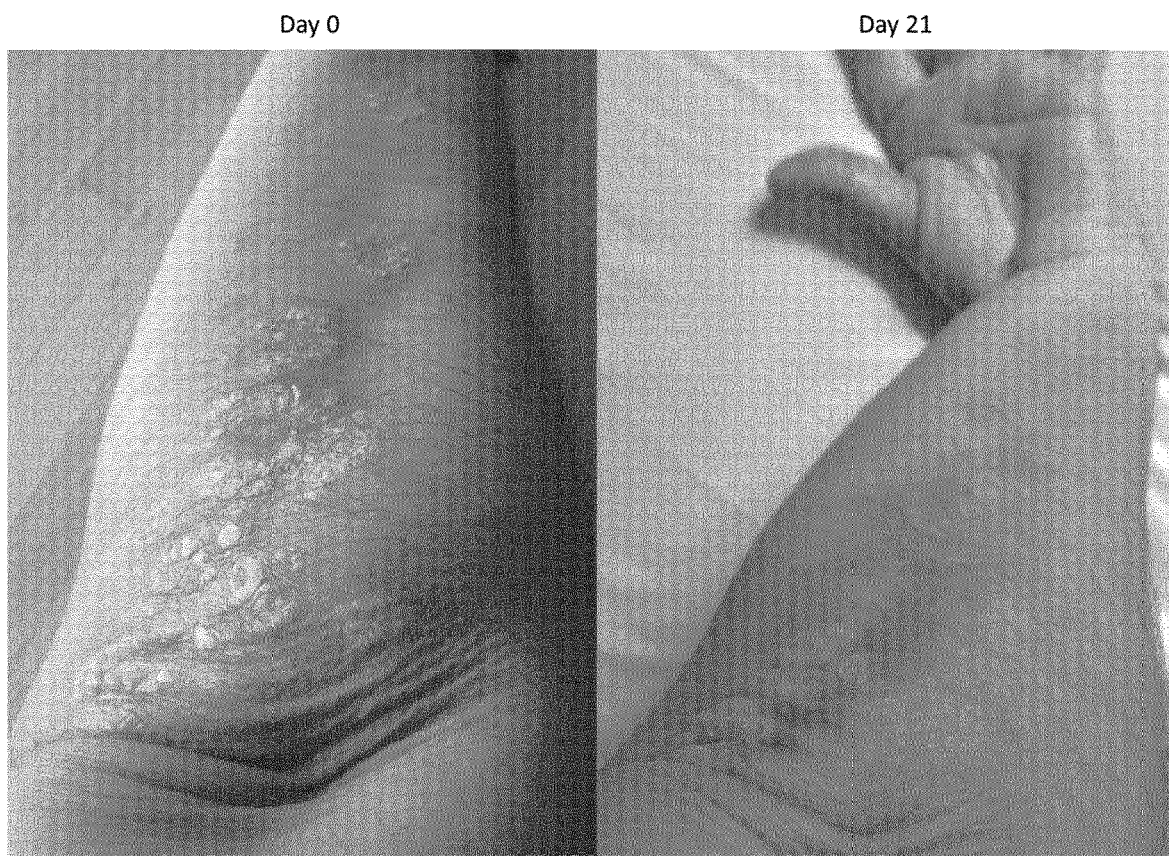
FIG. 8. 37 years old female treated with dog conditioned media. Images show the evolution of the psoriatic wounds during the 21 days that last the treatment in arm and foot. Peeling and scales diminish notably from the skin.
Figure 8:

After 21 days employing the conditioned media, skin peeling and scales diminished notably as shown in FIG. 8.

5$^{rd}$ Case. Treatment of Psoriasis in a Human Being 58 year old male. Diagnosed of psoriasis in the spring of 1980, with affected areas located in elbows.

Treatment of cream steroids in areas of major relevance without significant improvement. Change to treatment with petroleum/iodine preparation without positive effects (1981).

Change to Use of Acetylsalicylic Acid for years without further affecting scaling. (1982)

Punctual appearance on the scalps that appeared and disappeared and never in a critical or annoying state. (1990- . . . )

Abandonment of Acetylsalicylic acid and use of a moisturizer in areas of elbows, hands (1996-present).

We treated the lesions produced by the psoriasis for with dog conditioned media.

Figure 9:
FIG. 9. 58 years old human male treated with dog conditioned media. Images show the evolution of the psoriatic wounds during the 36 days that last the treatment in leg and hand. Peeling and scales disappear from the skin.
Figure 9:

After 36 days employing the conditioned media, skin peeling and scales diminished notably as shown in FIG. 9.

The invention claimed is:

1. A method of xenogenically treating atopic dermatitis in a human subject, the method comprising administering to the human subject having atopic dermatitis an amount of a composition comprising a conditioned cell culture medium effective for xenogenic treatment of atopic dermatitis in a human subject, the conditioned cell culture medium made by a process comprising:

culturing a population of mesenchymal stromal cells (MSCs) or immortalized cells obtained therefrom, in which at least 50% of said population by number of cells are MSCs obtained from a mammal of the genus *canis* or immortalized cells obtained therefrom, in a nutrient rich liquid or a basal media suitable for propagating the MSCs; and collecting the conditioned cell culture medium.

2. The method according to claim 1, wherein the MSCs are obtained from a dog species.

3. The method according to claim 1, wherein the MSCs are umbilical-cord derived stromal cells, adipose tissue-derived stromal cells, expanded mesenchymal stromal cells, expanded adipose tissue-derived stromal cells, bone-marrow derived stromal cells, expanded bone-marrow derived stromal cells, or immortalized mesenchymal stromal cells obtained therefrom.

4. The method according to claim 1, wherein the nutrient rich liquid prepared for cell culture is a buffered saline solution comprising amino acids and vitamins supplemented with sodium pyruvate and glutamine.

5. The method of claim 1, wherein the nutrient rich liquid is a basal media with supplementation.

6. The method of claim 1, wherein such composition is formulated to deliver an amount of conditioned medium at an appropriate interval to effectively treat atopic dermatitis.

7. The method according to claim 6, wherein such composition is formulated for administration by an intravenous, oral, or topical route.

8. The method of claim 7, wherein such route of administration is topical, and wherein the composition is a topical formulation that is formulated in liquid or in semi-solid form.

9. The method of claim 7, wherein such route of administration is topical, and wherein the composition is a topical formulation that is formulated in a form selected from a liquid, a fluid, a foam, a cream, a gel, a paste, a balsam, a spray, an ointment, a lotion, a conditioner, a tonic, a milk, a mousse, an emulsion, a serum, an oil, a stick, a shampoo, a jelly, a suspension, a dispersion, a lacquer, a paint, an elixir, a drop and an aerosol form.

10. The method of claim 7, wherein such route of administration is topical, and wherein the composition is a topical formulation that is formulated in a liposomal preparation.

* * * * *